United States Patent
Hsu et al.

(10) Patent No.: US 11,597,665 B2
(45) Date of Patent: Mar. 7, 2023

(54) DISINFECTION SYSTEM DEVICE FOR PRODUCING OZONE WATER DIRECTLY IN WATER PIPE SYSTEM

(71) Applicant: BIOTEK ENVIRONMENTAL SCIENCE LTD., New Taipei (TW)

(72) Inventors: Ming-Yung Hsu, New Taipei (TW); Gavin Hsu, New Taipei (TW)

(73) Assignee: BIOTEK ENVIRONMENTAL SCIENCE LTD., New Taipei (TW)

( * ) Notice: Subject to any disclaimer, the term of this patent is extended or adjusted under 35 U.S.C. 154(b) by 624 days.

(21) Appl. No.: 16/592,456

(22) Filed: Oct. 3, 2019

(65) Prior Publication Data
US 2021/0101810 A1    Apr. 8, 2021

(51) Int. Cl.
*C02F 1/78*      (2006.01)
*C25B 1/13*      (2006.01)
*A61L 2/18*      (2006.01)

(52) U.S. Cl.
CPC .................. *C02F 1/78* (2013.01); *C25B 1/13* (2013.01); *A61L 2/183* (2013.01)

(58) Field of Classification Search
CPC ...... C02F 1/78; C02F 1/32; C02F 1/48; C02F 1/72; C02F 1/46
See application file for complete search history.

(56) References Cited

U.S. PATENT DOCUMENTS 9,248,208 B2    2/2016    Li

FOREIGN PATENT DOCUMENTS

| CN | 106367777 A | * | 2/2017 | ............. C23C 20/08 |
| EP | 0608200 A1 | * | 7/1994 | ................ C02F 9/00 |

* cited by examiner

*Primary Examiner* — Walter D. Griffin
*Assistant Examiner* — Cameron J Allen
(74) *Attorney, Agent, or Firm* — Chun-Ming Shih; HDLS IPR Services

(57) ABSTRACT

A disinfection system device for producing ozone water directly in a water pipe system contains an electrolytic tap water ozonation generator and holder. The electrolytic tap water ozonation generator includes at least one anode sheet and at least one cathode sheet. The holder includes a base, and the base has a locking portion, an inflow orifice, an outflow orifice, a connection interface, and a damping valve. A flow switch is mounted above the base and has an intake, and a discharge orifice of the flow switch is communicated with the outflow orifice. A top of the base is connected with one of two lids, the other lid is connected with the first socket and a second socket, and the other lid accommodates a control panel. The number of the anode sheet(s) is n which is a natural number and n≥1. The number of the cathode sheets is n+1.

4 Claims, 4 Drawing Sheets

DISINFECTION SYSTEM DEVICE FOR
PRODUCING OZONE WATER DIRECTLY IN
WATER PIPE SYSTEM

FIELD OF THE INVENTION

The present invention relates to a disinfection system device for producing ozone water directly in a water pipe system.

BACKGROUND OF THE INVENTION

In general, fast food stores and beverage shops use water pipelines. For the safety of consumers, most of the water pipelines have activated carbon filters installed to remove residual chlorine in the water. Although this removes residual chlorine, bacteria and microorganisms are still easily found in the pipeline. One of the methods for solving bacteria and microorganisms in the pipeline is to use an electrolytic pure water ozone generator. The generated ozone gas is mixed with tap water to produce ozone water. For example, in U.S. Pat. No. 9,248,208 B2, ozone water flows into food and beverage facilities for water or ice machines to achieve the purpose of sterilization in the pipeline. However, such products, parts and processes that use an electrolytic pure water ozone generator and then mix ozone gas with tap water to generate ozone water are complicated and costly, and cannot be widely used. The present invention provides a disinfection system device for producing ozone water directly in a water pipe system for directly generating an ozone water disinfection system in a water pipe, which adopts an electrolytic tap water ozone generator. The present invention generates ozone gas microbubbles, which instantaneously dissolves and mix with tap water to directly generate ozone water, and the ozone water flows into the pipeline water; this achieves the device's purpose of sterilization. The device of the invention products and parts directly generate ozone water. Its application has simple process, low cost, and can be widely used.

SUMMARY OF THE INVENTION

The invention provides a disinfection system device for producing ozone water directly in a water pipe system. It adopts directly tap water for electrolysis to use in the ozone water generator, and the ozone gas microbubbles generated by the generator directly dissolve and mix with the tap water to generate ozone water directly at the moment of generation. The ozone water then flows into the water. This invention provides efficiently and cost-effective sterilization by using water already in the pipeline.
1. The invention provides a disinfection system device for producing ozone water directly in a water pipe system. It adopts an electrolytic tap water ozonation generator, the generator is connected to a constant current direct current power source. With this the tap water is electrolyzed under the action of an electric field, and the oxygen ions act on the anode catalyst. Next, ozone gas microbubbles are generated, and the ozone gas microbubbles are quickly dissolved into the tap water. This direct dissolution produces ozone water. The present invention and the electrolytic pure water ozone generator both generate ozone gas, then the ozone gas and the tap water are mixed to form ozone water. The method and the product and the parts are comparable to current ozone water generators, but the structure is simpler and the cost is lower.
2. The anode of the invention adopts electrolytic tap water ozonation generator is made of titanium plate and uses tin dioxide coating as anode. The process is simple and easy to scale production. For the anode plate of electrolytic pure water ozone generator is solved by using lead dioxide. Lead dioxide catalysts are prone to poisoning, loss of catalytic activity, and environmental pollution. Moreover, the cost of tin dioxide coating is also relatively low. The present invention uses tin dioxide for the anode coating.
3. The present invention uses electrolytic tap water ozonation generator. The present invention adopts the design of quick loading and quick unloading, making the generator easy to replace. It requires a simple manufacturing process and is convenient for service maintenance.
4. The present invention provides a disinfection system device for producing ozone water directly in a water pipe system, which uses a flow switch to sense changes in water flow and controls the time required to directly generate ozone water.

DETAILED DESCRIPTION OF THE PREFERRED EMBODIMENTS

Figure 1:
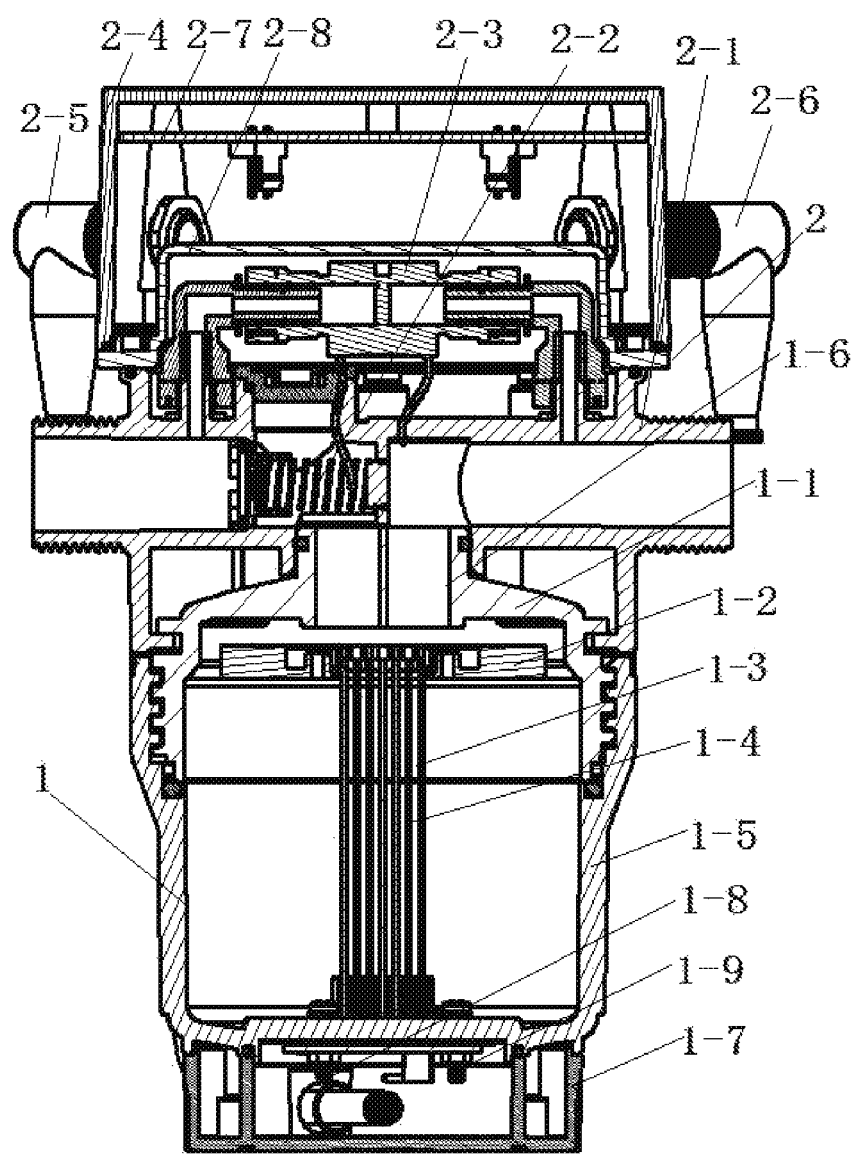
FIG. 1 is a perspective view showing the assembly of a disinfection system device for producing ozone water directly in a water pipe system according to the preferred embodiment of the present invention.
Figure 2:
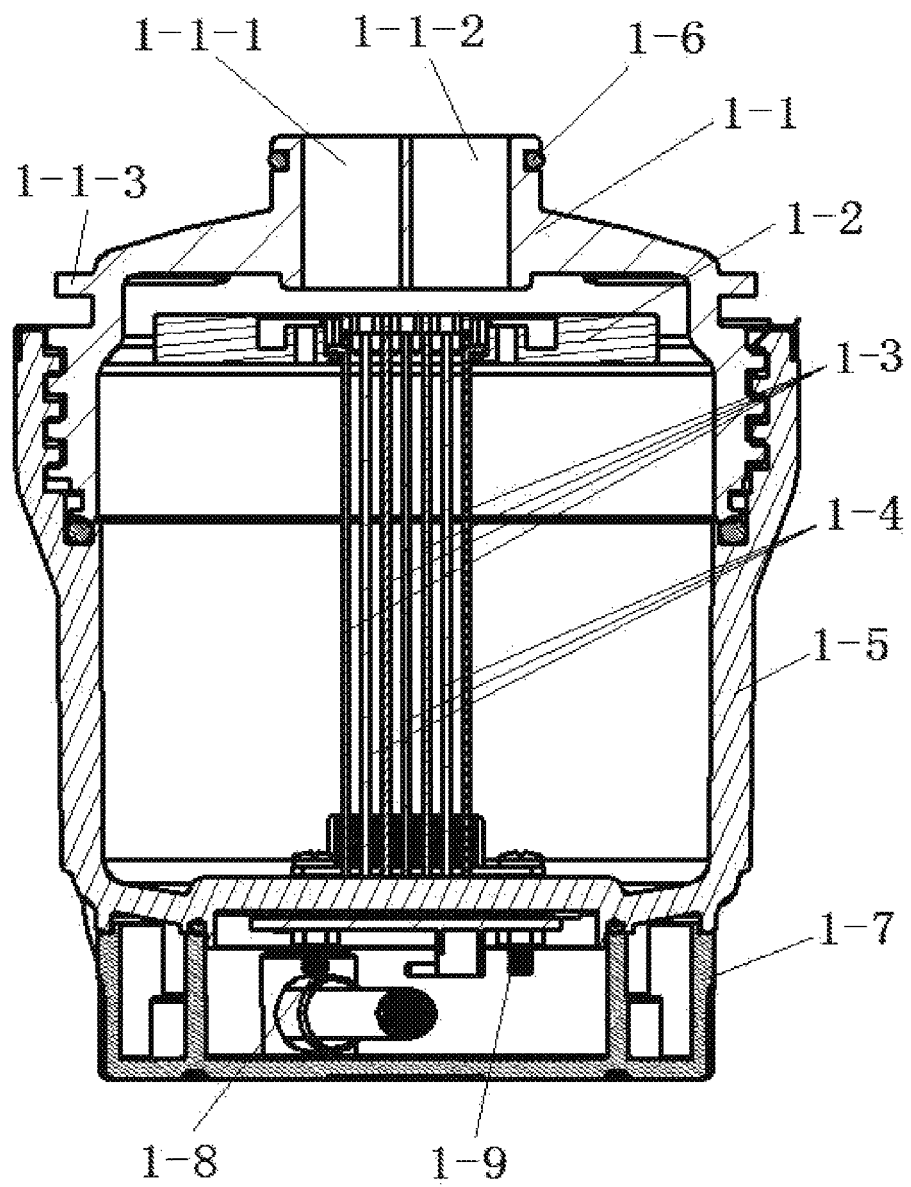
FIG. 2 is a perspective view showing the assembly of an electrolytic tap water ozonation generator as a component of the disinfection system device for producing ozone water directly in a water pipe system according to the preferred embodiment of the present invention.
Figure 3:
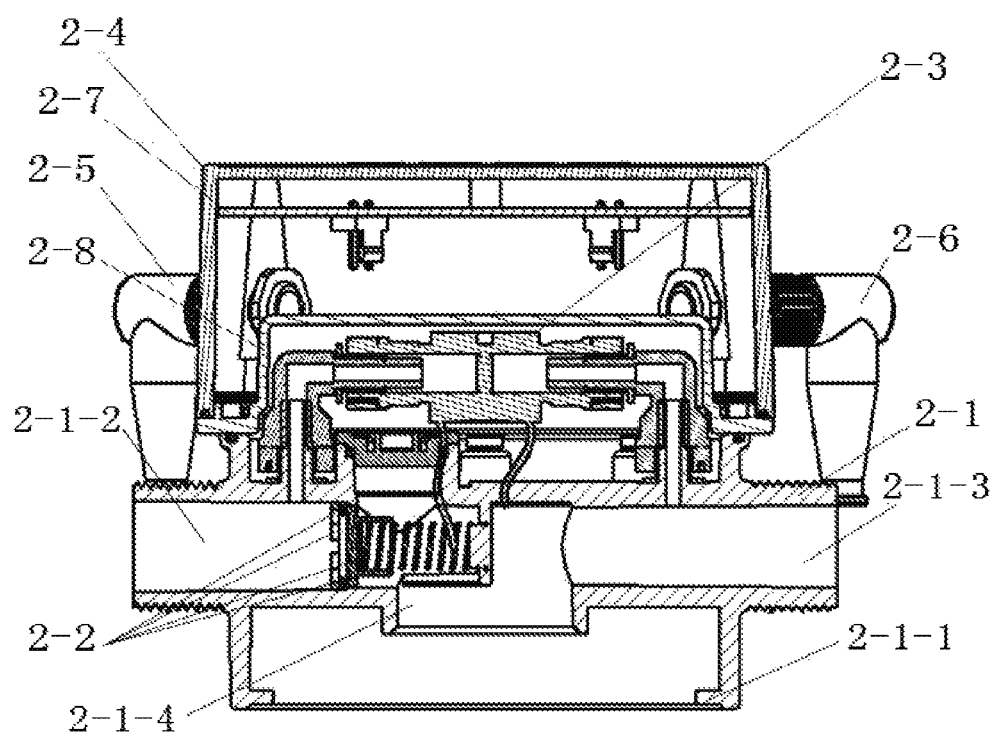
FIG. 3 is a perspective view showing the assembly of a holder of the disinfection system device for producing ozone water directly in a water pipe system according to the preferred embodiment of the present invention.
Figure 4:
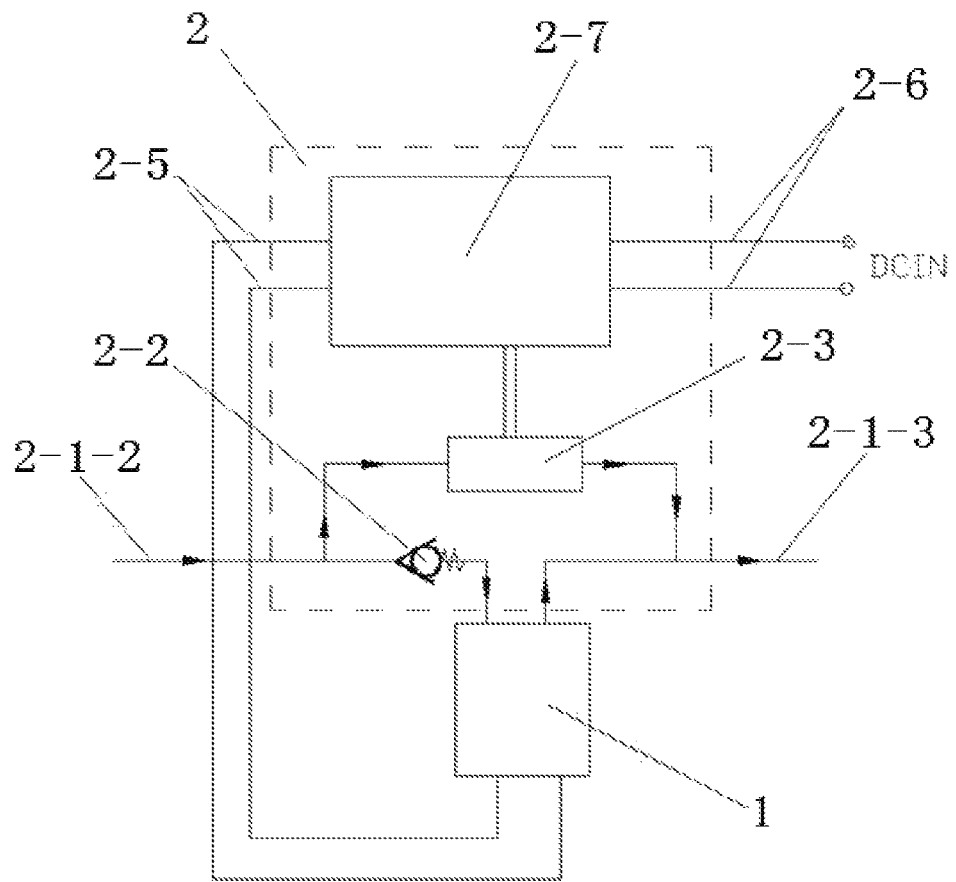
FIG. 4 is a schematic view of the disinfection system device for producing ozone water directly in a water pipe system according to the preferred embodiment of the present invention.

With reference to FIGS. 1-4), a disinfection system device for producing ozone water directly in a water pipe system according to the preferred embodiment of the present invention comprises an electrolytic tap water ozonation generator 1 and a holder 2 movably connected with the electrolytic tap water ozonation generator 1, wherein the electrolytic tap water ozonation generator 1 includes at least one anode sheet(s) 1-4 and at least one cathode sheet(s) 1-3, wherein the number of the anode sheet(s) 1-4 is n, and the number of the cathode sheets 1-3 is n+1, wherein the number n is a natural number which is greater than or equal to 1 (i.e., n≥1), and both the anode sheet 1-4 and the cathode sheets 1-3 are arranged separately so as to obtain the largest action area. The anode sheet(s) 1-4 is made of coated titanium anode, and the number n is at least one, cathode sheets 1-3 are made of metal titanium or stainless steel, in this embodiment, the cathode sheets 1-3 are made of the metal titanium. At least one bottom of the anode sheet(s) 1-4 is electrically connected, and at least one bottom of the cathode sheets 1-3 are electrically connected. The anode sheet(s) 1-4 and at cathode sheets 1-3 are fixed in a bucket 1-5 and are connected with a positive electrode and a negative electrode in the electrolytic tap water ozonation generator via an anode conductive stud 1-9 and a cathode conductive stud 1-8, and a cap 1-7 is mounted on the bottom of the bucket 1-5 so as to protect electrified components. A partition 1-2 is disposed on at least one top of the anode sheet(s) 1-4 and the cathode sheets 1-3 so as to avoid a short circuit of the anode sheet(s) 1-4 and the cathode sheets 1-3. A cover 1-1 is connected on top of the bucket 1-5 and includes an inlet 1-1-1 and an outlet 1-1-2. The bucket 1-5 accommodates the anode conductive stud 1-9 and the cathode conductive stud 1-8 which are connected with a first socket 2-5 for electrically connecting with the electrolytic tap water ozonation generator 1, wherein the anode sheet(s) 1-4 and the cathode sheets 1-3 are connected with the first socket 2-5 via the anode conductive stud 1-9 and the cathode conductive stud 1-8. The cover 1-1 further includes at least one fastener 1-1-3 formed thereon. The holder 2 includes a base 2-1, and the base 2-1 has at least one locking portion 2-1-1 formed on a bottom thereof, an inflow orifice 2-1-2 defined on a first end of the base 2-1, an outflow orifice 2-1-3 formed on a second end of the base 2-1, a connection interface 2-1-4 arranged on a bottom of a middle section of the base 2-1, and a damping valve 2-2 accommodated in the base 2-1. A flow switch 2-3 is mounted above the base 2-1 and has an intake communicating with the inflow orifice 2-1-2 via the water pipe system, and a discharge orifice of the flow switch 2-3 is communicated with the outflow orifice 2-1-3 of the base 2-1. A top of the base 2-1 is connected with a first lid 2-8 on which a second lid 2-4 is connected, wherein two sides of the second lid 2-4 are connected with the first socket 2-5 and a second socket 2-6 for electrically connecting with a power supply, and the second lid 2-4 accommodates a control panel 2-7 connected with the flow switch 2-3, wherein the control panel 2-7 is electrically connected with the power supply via the second socket 2-6, and the control panel 2-7 is electrically connected with the cathode conductive stud 1-8 and the anode conductive stud 1-9 via the first socket 2-5. When the electrolytic tap water ozonation generator 1 is inserted into the holder 2, i.e., the cover 1-1 of the electrolytic tap water ozonation generator 1 is inserted into the connection interface 2-1-4 of the base 2-1, and the fastener 1-1-3 of the electrolytic tap water ozonation generator 1 is fastened with the locking portion 2-1-1 of the base 2-1. Then, an O-ring 1-6 seals the fastener 1-1-3 and the locking portion 2-1-1, and the inlet 1-1-1 and the outlet 1-1-2 are communicated with the connection interface 2-1-4 of the holder 2.

The anode sheet(s) and the cathode sheets 1-3 are immersed in water with an electrical conductivity of more than 30 μs/cm. Constant currents are then supplied to the anode sheet(s) 1-4 and at least one cathode sheet 1-3, wherein a supply of constant current is within 3.5 V to 12 V. The tap water is electrolyzed by an electric field, oxygen ion produces ozone and ozone microbubbles by ways of anode catalyst, and the ozone microbubbles dissolve and mix in the tap water to produce ozone water.

After supplying water and power source to the tap water pipe system and the disinfection system device respectively, for example, when the water flows into the water pipe system and its electrical conductivity is more than 30 μs/cm, the water flows into the outflow orifice 2-1-3 and the generator from the inflow orifice 2-1-2 via the flow switch 2-3, the damping valve 2-2, and the inlet 1-1-1 respectively, in which a part of the water in the flow switch 2-3 is sufficient by using the damping valve 2-2, and a signal of the flow switch 2-3 is sent to the control panel 2-7 so that the control panel 2-7 supplies the constant currents to the ozone water generator 1 via the first socket 2-5, the cathode conductive stud 1-8, and the anode conductive stud 1-9, such that the electrolytic tap water ozonation generator 1 operates within 3.5 V to 12 V. The tap water is electrolyzed by the electric field, the oxygen ion produces the ozone and the ozone microbubbles by way of the anode catalyst, and the ozone microbubbles dissolve and mix in the tap water to produce the ozone water directly. The ozone water flows into the water pipe system to eliminate biofilms and to sterilize via the outlet 1-1-2 and the outflow orifice 2-1-3. When the water stops flowing in the water pipe system, the control panel 2-7 receives a stop signal to stop supplying the power source to the electrolytic tap water ozonation generator 1. When desiring to produce ozone water of high concentration in a next using cycle time, the control panel 2-7 supplies the constant currents to the electrolytic tap water ozonation generator 1 for a period of time and then stops supplying constant current. Preferably, the control panel 2-7 supplies constant current to the electrolytic tap water ozonation generator for 5 minutes so as to store the ozone water of high concentration in the electrolytic tap water ozonation generator 1, and the ozone water of high concentration is supplied instantly in the next using cycle time.

The coated titanium anode is manufactured by using following methods:

In first embodiment, a punched titanium substrate of 1000 $cm^2$ is provided, wherein a thickness of the punched titanium substrate is 1 mm. A diameter of each of multiple apertures on the punched titanium substrate is 3 mm, an arrangement density of the multiple apertures is one aperture/per square centimeter. The punched titanium substrate is surface blasted and is placed into hydrochloric acid solution, with a volume percentage concentration of the hydrochloric acid solution is 30%. The punched titanium substrate is heated to a temperature of 90° C. and is etched in the hydrochloric acid solution for 5 minutes.

Then, the punched titanium substrate is washed by pure water after being etched and is placed into another hydrochloric acid solution, with a volume percentage concentration of 3%.

Prepare 30 grams of stannic chloride pentahydrate, 3.9 grams of ruthenium chloride consisting of 37% ruthenium, and 1.13 grams of nickel chloride hexahydrate are prepared. These are dissolved into a solution consisting of 30.9 ml of butyl titanate, 9 ml of nitric acid, and 300 ml of ethanol are mixed to produce tin dioxide coating solution consisting of ruthenium and nickel. After removing and drying the punched titanium substrate, a coating material (i.e., the tin dioxide coating solution) is coated on the punched titanium substrate and is baked to dry in an infrared oven in a temperature at 120° C. for six minutes. Then, the punched titanium substrate is placed and heated in a high temperature furnace in a temperature of 420° C. for ten minutes so as to decompose the coating material. After repeating 8 times of applying, baking, and decomposing steps, the high temperature furnace is adjusted to a temperature of 500° C. so as to decompose the coating material of the punched titanium substrate for two hours, and the punched titanium substrate is removed, thus finishing the coated titanium anode.

In the second embodiment, a titanium substrate of 1000 $cm^2$ is provided, wherein a thickness of the titanium substrate is 0.6 mm. The titanium substrate is surface blasted and is placed into hydrochloric acid solution, wherein a volume percentage concentration of the hydrochloric acid solution is 20%. The titanium substrate is heated to a temperature of 90° C. and is etched in the hydrochloric acid solution for 8 minutes. Then, the titanium substrate is washed by pure water after being etched and is placed into another hydrochloric acid solution, with a volume percentage concentration of 2%.

Then, 30 grams of stannic chloride pentahydrate, 3 grams of ruthenium chloride consisting of 37% ruthenium, and 0.5 grams of nickel chloride hexahydrate into solution consisting of 20 ml of butyl titanate, 5 ml of nitric acid, and 300 ml of ethanol are prepared. After removing and drying the titanium substrate, a coating material (i.e., the tin dioxide coating solution) consisting of ruthenium and nickel is coated on the titanium substrate, and the titanium substrate is baked to dry in an infrared oven at temperature of 130° C. for three minutes. Then, the titanium substrate is placed and heated in a high temperature furnace in a temperature of 400° C. for fifteen minutes so as to decompose the coating material. After repeating 12 times of applying, baking, and decomposing steps, the high temperature furnace is adjusted to a temperature of 480° C. so as to decompose the coating material of the titanium substrate for three hours, and the titanium substrate is removed, thus finishing the coated titanium anode.

In the third embodiment, a titanium mesh of 1000 cm$^2$ is provided, wherein the titanium mesh is stretched by 4 mm×6 mm. The titanium mesh is surface blasted and is placed into hydrochloric acid solution, wherein a volume percentage concentration of the hydrochloric acid solution is 10%. The titanium mesh is heated to a temperature of 90° C. and is etched in the hydrochloric acid solution for 8 minutes. Then, the titanium mesh is washed by pure water after being etched and is placed into another hydrochloric acid solution, a volume percentage concentration of which is 1%.

Then, 30 grams of stannic chloride pentahydrate, 2.34 grams of ruthenium chloride consisting of 37% ruthenium, and 0.204 grams of nickel chloride hexahydrate into solution consisting of 9.09 ml of butyl titanate, 3 ml of nitric acid, and 300 ml of ethanol are prepared. After removing and drying the titanium mesh, a coating material (i.e., the tin dioxide coating solution) consisting of ruthenium and nickel is coated on the titanium mesh and is baked to dry in an infrared oven at a temperature of 90° C. for ten minutes. Then, the titanium mesh is placed and heated in a high temperature furnace in a temperature of 450° C. for eight minutes so as to decompose the coating material. After repeating 5 times of applying, baking, and decomposing steps, the high temperature furnace is adjusted to a temperature of 520° C. so as to decompose the coating material of the titanium mesh for one hour, and the titanium mesh is removed, thus finishing the coated titanium anode.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A disinfection system device for producing ozone water directly in a water pipe system comprising an electrolytic tap water ozonation generator (1) and a holder (2) movably connected with the electrolytic tap water ozonation generator (1):

wherein the ozone water generator (1) includes at least one anode sheet (1-4) and a plurality of cathode sheets (1-3), wherein a number of the anode sheet(s) (1-4) is n, and a number of cathode sheets (1-3) is n+1, wherein the number n is a natural number which is greater than or equal to 1, wherein the anode sheet(s) (1-4) is made of coated titanium anode, and the cathode sheets (1-3) are made of metal titanium or stainless steel;

wherein the holder (2) includes a base (2-1), and the base (2-1) has a locking portion (2-1-1) formed on a bottom thereof, an inflow orifice (2-1-2) defined on a first end of the base (2-1), an outflow orifice (2-1-3) formed on a second end of the base (2-1), a connection interface (2-1-4) arranged on a bottom of a middle section of the base (2-1); wherein a damping valve (2-2) is accommodated in the base (2-1), a flow switch (2-3) is mounted above the base (2-1) and has an intake communicating with the inflow orifice (2-1-2) via the water pipe system; and a discharge orifice of the flow switch (2-3) is communicated with the outflow orifice (2-1-3) of the base (2-1) via the water pipe system, a top of the base (2-1) is connected with a first lid (2-8), wherein two sides of a second lid (2-4) are connected with the first socket (2-5) and a second socket (2-6) for electrically connecting with a power supply, and the second lid (2-4) accommodates a control panel (2-7) connected with the flow switch (2-3); wherein the control panel (2-7) is electrically connected with the power supply via the second socket (2-6), and the control panel (2-7) is electrically connected with the anode sheet(s) (1-4) and the cathode sheets (1-3) via the first socket (2-5).

2. The disinfection system device as claimed in claim 1, wherein the anode sheet(s) (1-4) and the cathode sheets (1-3) are vertical arranged separately; the anode sheet(s) (1-4) and the cathode sheets (1-3) are fixed in a bucket (1-5), and a cap (1-7) is mounted on the bottom of the bucket (1-5), a partition (1-2) is disposed at the top of the anode sheet(s) (1-4) and the cathode sheets (1-3), a cover (1-1) is affixed on top of the bucket (1-5) and includes an inlet (1-1-1) and an outlet (1-1-2); the bucket (1-5) accommodates an anode conductive stud (1-9) and a cathode conductive stud (1-8) which are connected with the first socket (2-5) for electrically connecting with the electrolytic tap water ozonation generator (1), wherein the anode sheet(s) (1-4) and the cathode sheets (1-3) are connected with the first socket (2-5) via the anode conductive stud (1-9) and the cathode conductive stud (1-8).

3. The disinfection system device as claimed in claim 2, wherein the cover (1-1) of the electrolytic tap water ozonation generator (1) is inserted into the connection interface (2-1-4) of the base (2-1), the inlet (1-1-1) and the outlet (1-1-2) are communicated with the connection interface (2-1-4) of the holder (2); the cover (1-1) further includes at least one fastener (1-1-3) formed thereon, the holder (2) includes at least one locking portion (2-1-1) for engaging with the at least one fastener (1-1-3) respectively.

4. The disinfection system device as claimed in claim 1, wherein the coated titanium anode of the anode sheet(s) (1-4) consists of a titanium substrate and a tin dioxide coating layer consisting of ruthenium and nickel, in a tin dioxide coating layer.

* * * * *